United States Patent [19]

Merger et al.

[11] Patent Number: 4,837,357

[45] Date of Patent: Jun. 6, 1989

[54] PREPARATION OF 2,2-DISUBSTITUTED 3-CHLOROPROPIONIC ESTERS

[75] Inventors: Franz Merger, Frankenthal; Peter Hettinger, Edingen-Neckarhausen, both of Fed. Rep. of Germany

[73] Assignee: BASF Aktiengesellschaft, Ludwigshafen, Fed. Rep. of Germany

[21] Appl. No.: 111,624

[22] Filed: Oct. 21, 1987

[30] Foreign Application Priority Data

Nov. 7, 1986 [DE] Fed. Rep. of Germany ....... 3638009

[51] Int. Cl.[4] ............................................. C07C 69/63
[52] U.S. Cl. ................................... 560/226; 260/408; 549/346; 549/347; 549/378; 549/425; 549/450; 549/484; 560/105; 560/106; 560/112; 560/122; 560/184; 560/219
[58] Field of Search ............... 549/346, 347, 378, 425, 549/450, 484; 560/226, 228, 230, 113, 122, 125, 105, 103, 184, 219, 106, 112; 260/408

[56] References Cited

U.S. PATENT DOCUMENTS 3,852,335 12/1974 Merger et al. .
4,334,083 6/1982 Buathier et al. ..................... 560/226
4,408,068 10/1983 Koch .................................... 560/226

FOREIGN PATENT DOCUMENTS 234358 3/1974 Fed. Rep. of Germany .
2500311 7/1976 Fed. Rep. of Germany .
34325 7/1986 Fed. Rep. of Germany .
152461 2/1978 United Kingdom .

Primary Examiner—Werren B. Lone
Attorney, Agent, or Firm—John H. Shurtleff

[57] ABSTRACT

2,2-Disubstituted 3-chloropropionic esters I

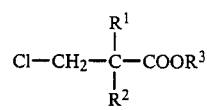

where $R^1$ and $R^2$ are each $C_1$-$C_6$-alkyl, $C_2$-$C_6$-oxaalkyl, $C_2$-$C_6$-alkenyl, $C_2$-$C_6$-oxaalkenyl, aryl or $C_7$-$C_{12}$-aralkyl or $R^1$-C-$R^2$ is 5-, 6- or 7-membered ring, $R^3$ is $C_2$-$C_6$-oxaalkyl, $C_2$-$C_6$-alkenyl, $C_2$-$C_6$-oxaalkenyl or $C_7$-$C_{12}$-aralkyl, are prepared by converting 2,2-disubstituted 3-hydroxypropanals II

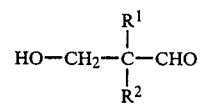

into the esterdiol III

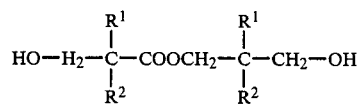

reacting this esterdiol III in the presence of a transesterification catalyst with an alcohol $R^3OH$ to give the 3-hydroxyester IV

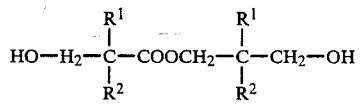

reacting the hydroxyester IV with a stoichiometric or greater than stoichiometric amount of the thionyl chloride and thermally decomposing the product to give the chloropropionic ester I.

11 Claims, No Drawings

PREPARATION OF 2,2-DISUBSTITUTED 3-CHLOROPROPIONIC ESTERS

The present invention relates to a novel process for preparing a 2,2-disubstituted 3-chloropropionic ester of the formula I

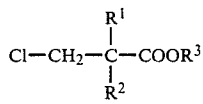

where $R^1$ and $R^2$ are each $C_1$–$C_6$-alkyl, $C_2$–$C_6$-oxaalkyl, $C_2$–$C_6$-alkenyl, $C_2$–$C_6$-oxaalkenyl, aryl or $C_7$–$C_{12}$-aralkyl, where $R^1$-C-$R^2$ together can also be a 5-, 6- or 7-membered ring, and where $R^3$ has the meanings of $R^1$ and $R^2$ other than aryl.

The prior art method of preparing 2,2-disubstituted 3-chloropropionic esters, which are useful intermediates for preparing isoxazolidin-3-ones which are used as building blocks for crop protection agents, is to esterify appropriately substituted 3-chloropropionic acids of 3-chloropropionyl chlorides. However, this pathway is relatively expensive and of little commercial interest since the starting materials are not readily accessible. In fact, chloropropionic acids, for example, are obtainable only within narrow limits by the known monochlorination of neocarboxylic acids, which is difficult to control and affected by corrosion problems.

It is an object of the present invention to make possible the preparation of 2,2-disubstituted 3-chloropropionic esters I from inexpensive, readily available starting materials in a wider range of variation.

We have found that this object is achieved in a process for preparing a 2,2-disubstituted 3-chloropropionic ester of the formula I

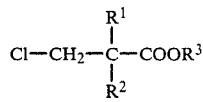

where $R^1$ and $R^2$ are each $C_1$–$C_6$-alkyl, $C_2$–$C_6$-oxaalkyl, $C_1$–$C_6$-alkenyl, $C_2$–$C_6$-oxaalkenyl, aryl or $C_7$–$C_{12}$-aralkyl, where $R^1$-C-$R^2$ together can also form a 5-, 6- or 7-membered ring, and where $R^3$ has the meanings of $R^1$ and $R^2$ other than aryl, which comprises converting a 2,2-disubstituted 3-hydroxypropanal of the formula II

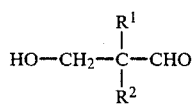

into the esterdiol III

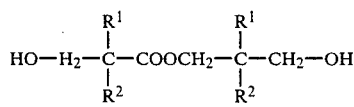

reacting this esterdiol III in the presence of a transesterification catalyst with an alcohol $R^3OH$ to give the 3-hydroxyester IV

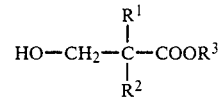

and reacting the hydroxyester IV with a stoichiometric or greater than stoichiometric amount of thionyl chloride to give the chloropropionic ester I.

The overall process can be represented by the following reaction equations:

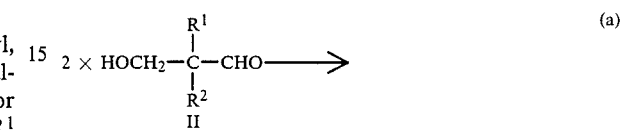

(a)

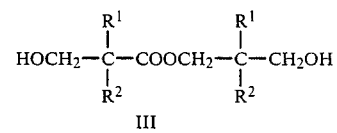

III

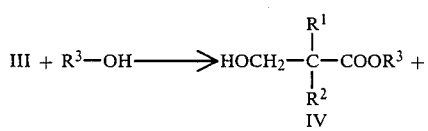

(b)

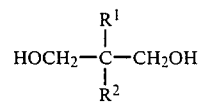

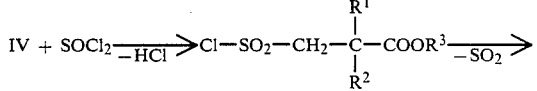

(c)

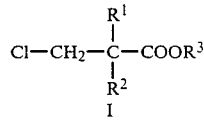

I

Using this process, it is possible to prepare the end product I in good yield (up to over 70%, based on starting material II). The success of the process is surprising since both step (b) and step (c) would be expected to give rise to secondary reactions, owing to the structure of esters III and IV. For instance, in the case of the transesterification reaction (b) it had to be assumed that the alcohol groups in the esterdiol III would compete with the added alcohol $R^3OH$, leading to oligoester and polyester formation. From the prior art it had to be assumed that the replacement of the hydroxyl group by chlorine in step (c) would at most proceed in an unsatisfactory yield, owing to the sterically hindered structure of IV. For instance, J. Chem. Soc. 3640–3641 (1954) reveals that the thermal decomposition of neopentyl chlorosulfinate in the presence of quinoline hydrochloride at 115° C. to give neopentyl chloride takes place in a yield of only 47%.

The starting material II required for the process according to the invention is readily accessible, for example by aldol reaction of a 2,2-disubstituted acetaldehyde with formaldehyde (see Houben-Weyl, Methoden der organischen Chemie, Vol. 7.1, pp. 89 (1954) or as described in German Laid-Open Applications DOS No. 1,793,512 and DOS No. 1,957,301 and also by reacting a 2-alkylacrolein with an alcohol and formaldehyde as described in German Laid-Open Application DOS No. 3,321,517. Suitable $R^1$ and $R^2$ are $C_1-C_6$-alkyl, $C_2-C_6$-oxaalkyl, $C-C_6$-alkenyl, $C_2-C_6$-oxaalkenyl, aryl and $C_7-C_{12}$-aralkyl. Specific examples are methyl, ethyl, propyl, isopropyl, butyl, pentyl, hexyl, methoxymethyl, ethoxymethyl, methoxyethyl and isopropoxyethyl on the one hand and allyl, phenyl, phenylethyl and benzyl on the other. $R^1$ and $R^2$ can also together be a 5-, 6- or 7-membered ring which may contain one or more, in particular 1 or 2, oxygen atoms; for example, $R^1$ and $R^2$ can be together with the carbon atom to which they are bonded cyclopentyl, cyclohexen-3-yl, cyclohexyl, tetrahydrofur-2-yl, tetrahydropyran-2-yl or 1,4-dioxacyclohexyl. Preferably, $R^1$ is $C_1-C_6$-alkyl and $R^2$ is $C_1-C_6$-alkyl, $C_1-C_6$-oxaalkyl, phenyl or benzyl, or $R^1$ and $R^2$ are together $C_5-C_7$-cycloalkyl which may contain 1 or 2 oxygen atoms.

The preparation of ester III by disproportionation of starting material II by the method of Tischenko can be effected in a conventional manner, for example by heating a 2,2-disubstituted 3-hydroxypropanal in the presence or absence of a catalyst, preferably by the methods described in German Laid-Open Applications DOS No. 2,234,358, DOS No. 2,500,311 and DOS No. 3,432,577. In a preferred, commercially particularly advantageouus embodiment of the process, the product III is directly used without purification, if necessary after unconverted starting material has been separated off.

Stage (b) of the process can be carried out in the presence of a conventional transesterification catalyst, for example an alcoholate. Particularly preferred catalysts are alkaline earth metal or in particular alkali metal alcoholates, for example magnesium alcoholates, calcium alcoholates, lithium alcoholates, sodium alcoholates or potassium alcoholates, the choice of alcohol component being substantially open. It is thus preferable to use a $C_1-C_8$-alcoholate, advantageously an alcoholate corresponding to the alcohol $R^3OH$ used.

The alcohol $R^3OH$ used is preferably methanol if the end product is to be converted into an isoxazolidinone. Furthermore, $R^3$ can be $C_1-C_6$-alkyl, $C_2-C_6$-oxaalkyl, $C_2-C_6$-alkenyl, $C_2-C_6$-oxaalkenyl or $C_7-C_{12}$-aralkyl. Specific examples are methanol, ethanol, propanol, isopropanol, n-butanol, iso-butanol, tert.-butanol, n-pentanol, iso-pentanol, n-hexanol, iso-hexanol, methoxyethanol, butoxyethanol, allyl alcohol and methallyl alcohol. Aralkyl alcohols are for example benzyl alcohol and 2-phenylethan-1-ol.

The transesterification can be carried out at from $-10°$ to $+50°$ C., preferably from $10°$ to $40°$ C., in particular from $20°$ to $35°$ C. The amount used of alcohol $R^3OH$ is basically not critical and can range from 1 to 20 moles, advantageously from 2 to 15 moles, in particular from 5 to 12 moles, per mole of esterdiol III. The base is only required in a catalytic amount. In the case of alkali metal alcoholates, it is preferable to use from 0.01 to 0.1 mole per mole of esterdiol III. Especially if the amount of $R^3OH$ used lies towards the lower end of the acceptable molar ratio, the removal of unconverted esterdiol and recycling thereof can be advisable. The products can advantageously be isolated from the reaction mixture by distillation in a conventional manner.

The 2,2-disubstituted 3-hydroxyester IV thus obtained is converted by reaction with a stoichiometric or greater than stoichiometric amount of thionyl chloride into the chloropropionic ester I. Advantageously, it is possible to use from 1 to 3 moles of thionyl chloride per mole of IV; higher amounts are possible but do not produce any extra benefit.

The reaction of IV with thionyl chloride is preferably carried out within 2 temperature ranges by first substantially converting to the chlorosulfinate at from $-10°$ to $60°$ C., preferably from $0°$ to $60°$ C., in particular from $10°$ to $50°$ C., and then raising the temperature as high as $180°$ C. Before thermocleaving the chlorosulfinate intermediate it is advantageous to separate off any excess thionyl chloride present in the reaction mixture by distillation.

The cleaving of the chlorosulfinate into $SO_2$ and chloropropionic ester I can be carried out in the presence of a catalytic amount of a tertiary nitrogen base such as pyridine, quinoline or dimethylaniline or a salt thereof, for example a hydrochloride. In general, the temperatures are within the range from $120°$ to $180°$ C., in particular from $120°$ to $140°$ C.

The process according to the invention makes possible, starting from readily accessible starting materials, a commercial production of 2,2-disubstituted 3-chloropropionic esters which are useful as intermediates for plant protection agents. The substituted 1,3-propanediols obtained as a by-product in stage (b) of the process are in general additional useful products; for example, neopentyl glycol can be used as a component for polyesters or polyurethanes.

EXAMPLE 1

Preparation of methyl 2,2-dimethyl-3-chloropropionate 101 g (1.25 mol) of 37% strength aqueous formaldehyde solution and 99 g (1.37 mol) of isobutyraldehyde were mixed at $40°$ C. under nitrogen with 4.2 g (0.03 mol) of 40% strength aqueous trimethylamine solution by stirring. The temperature of the mixture rose to $93°$ to $94°$ in the course of from 15 to 20 minutes. The mixture was stirred at that temperature for a further 10 minutes, and the trimethylamine, excess isobutyraldehyde and 58 g of water were then distilled off under reduced pressure. The remaining solution of hydroxypivalinaldehyde was then cooled down to $60°$ C., and 1.9 g (0.025 mol) of finely pulverulent calcium hydroxide were then added with vigorous stirring. After the exothermic reaction had ceased and a further, short period of stirring, 2.5 g (0.054 mol) of 100% strength formic acid were added at $70°$ C., and the mixture was stirred $70°$ C. for 10 minutes. The aqueous phase was then separated off, and the organic phase was subjected to fractional distillation. 110 g (0.54 mol) were isolated of 2,2-dimethyl-1,3-propanediol hydroxypivalate, corresponding to 86.5% of theory, based on starting formaldehyde.

136 g (0.66 mol) of 2,2-dimethyl-1,3-propanediol hydroxypivalate were disolved in 149 ml of methanol, 1.3 g (0.02 mol) of sodium methanolate were added, and the mixture was stirred at room temperature for 16 h.

The reaction mixture was then neutralized with acetic acid and worked up by fractional distillation. After the methanol had been separated off, 78 g (0.59 mol) were obtained of methyl hydroxypivalate having a boiling point of $135°$ C./175 mbar and 58 g (0.56 mol) of 2,2-dimethyl-1,3-propanediol, which corresponds to a yield of 89 and 84.5% respectively, based on starting esterdiol.

132 g (1 mol) of methyl hydroxypivalate were added to 238 g (2 mol) of thionyl chloride with cooling at such a rate that the temperature of the reaction mixture did not exceed 20° C. After the addition was complete, the mixture was stirred at 50° C. for 1 h. Excess thionyl chloride was then distilled off under atmospheric pressure, 0.2 g (0.0025 mol) of pyridine was added to the residue, and the mixture was heated to 135° C.

After the evolution of $SO_2$ had ended, isolation by distillation gave 138 g (0.92 mol) of methyl 2,2-dimethyl-3-chloropropionate (boiling point 82° C./5 mbar) in a 92% yield, based on methyl hydroxypivalate.

EXAMPLE 2

120 g (1.18 mol) of triethylamine were added with vigorous stirring under reflux to a hot mixture at 50° C. of 975 g (12 mol) of 37% strength formaldehyde solution and 865 g (12 mol) of isobutyraldehyde, and the mixture was allowed to rise to 92° to 94° C. in the course of 10 minutes. Triethylamine and water were then distilled off at from 150 to 30 mbar in the course of from 15 to 20 minutes and at a maximum bottom of column temperature of from 70° to 75° C. The remaining mixture was then heated under atmospheric pressure to 160° C. in the course of 15 minutes, during which, essentially, further residues of water came off, and was stirred at that temperature for a further 160 minutes. Distillation of the mixture gave 180 g of a fraction of boiling range 80°–95° C. at 8–10 mbar, which contained 119 g (1.17 mol) of hydroxypivalinaldehyde, corresponding to 9.75%, based on the starting materials. This left a residue of 305 g which, according to analysis by gas chromatography, comprised 96% (869 g; 4.26 mol) of 2,2-dimethylpropane-1,3-diol hydroxypivalate, corresponding to a 71% yield, based on the starting materials (overall selectivity 80.75%). The residue was taken up in 1,100 ml of methanol, 15 g (0.28 mol) of sodium methanolate were added, and the mixture was stirred at room temperature for 15 hours. Neutralization with acetic acid and fractional distillation gave 496.5 g (3.76 mol) of methyl hydroxypivalate, corresponding to 88.34% yield, based on esterdiol III, and also 375.4 g (3.68 mol) of 2,2-dimethyl-1,3-propanediol, corresponding to an 86.4% yield.

Methyl hydroxypivalate was added at below 20° C. to 893 g (7.5 mol) of thionyl chloride, and the mixture was stirred at 50° C. for 1 hour. Excess thionyl chloride was then distilled off under atmospheric pressure, 1 g (0.0125 mol) of pyridine was added to the residue, and the temperature was raised to 135° C.

After the evolution of $SO_2$ had ended, isolation by distillation gave 524.8 g (3.48 mol) of methyl 2,2-dimethyl-3-chloropropionate (boiling point 82° C./5 mbar), corresponding to a 92.7% yield, based on methyl hydroxypivalate.

EXAMPLE 3

232 g (2 mol) of 2-methyl-2-ethyl-3-hydroxypropanal and 12 g of water were heated to 50° C., and 4.5 g (0.06 mol) of calcium hydroxide were added. After the exothermic reaction had ceased, the mixture was stirred at 70° C. for 30 min and then neutralized with formic acid, and the salt was removed by aqueous extraction. The product mixture was then distilled at up to the boiling point of 2-methyl-2-ethyl-1,3-propanediol 2-methyl-2-ethyl-3-hydroxypropionate (140°–142° C.) to give a first cut of 42 g.

The residue was then taken up in 240 ml of methanol, 2.5 g (0.046 mol) of sodium methylate were added, and the mixture was stirred at room temperature for 16 h. After neutralization with acetic acid, fractional distillation gave 108.9 g (0.74 mol) of methyl 2-methyl-2-ethyl-3-hydroxypropionate having a boiling point of 100° C./30 mbar, corresponding to a 74.6% yield, based on starting 2-methyl-2-ethyl-3-hydroxypropanal, and also 89.7 g of 2-methyl-2-ethyl-1,3-propanediol, corresponding to a 76% yield.

The methyl 2-methyl-2-ethyl-3-hydroxypropionate was added at below 20° C. to 178.6 g (1.5 mol) of thionyl chloride, and the mixture was stirred at 50° C. for a further 30 min. Excess thionyl chloride was then distilled off at 100 mbar, 0.5 g (0.006 mol) of pyridine was added to the residue, and the mixture was heated at from 130° to 135° C. for 45 min. Fractional distillation gave 114.4 g of methyl 2-methyl-2-ethyl-3-chloropropionate having a boiling point of 101°–104° C./8 mbar, corresponding to a 93.2% yield, based on methyl 2-methyl-2-ethyl-3-hydroxypropionate. The overall yield was 69.5%, based on 2-methyl-2-ethyl-3-hydroxypropanal.

EXAMPLE 4

430 g (3 mol) of 1-hydroxymethylcyclohexylaldehyde were reacted at 95° C. with 7 g (0.095 mol) of pulverulent calcium hydroxide as described in Example 3. 100 g of water and 10 g of formic acid were then added, and the salt was removed by aqueous extraction. The product mixture was then distilled at up to the boiling point of 1,1-bis-hydroxymethylcyclohexane 1'-hydroxymethylcyclohexanecarboxylate (196°–198° C./3 mbar) to give a first cut of 69 g.

The residue was taken up in 350 ml of methanol, 3.75 g (0.069 mol) of sodium methanolate were added, and the mixture was stirred at room temperature for 15 hours. After neutralization with acetic acid, fractional distillation gave 179.8 g (1.046 mol) of methyl 1-hydroxymethylcyclohexanecarboxylate having a boiling point of 105°–115° C./1–2 mbar, corresponding to a 69.7% yield, based on starting 1-hydroxymethylcyclohexylaldehyde.

The hydroxyester is reacted as described in Example 3 with 238 g (2 mol) of thionyl chloride and the product is heated to 135° C. in the presence of 1 g (0.0125 mol) of pyridine. After the evolution of $SO_2$ had ended, isolation by distillation gave 187.3 g (0.98 mol) of methyl 1-chloromethylcyclohexanecarboxylate of boiling point 95°–110° C./12 mbar, corresponding to a 65.3% yield, based on converted 1-hydroxymethylcyclohexylaldehyde.

EXAMPLE 5

37.5 g (0.51 mol) of calcium hydroxide were added to a hot mixture at 60° C. of 750 g (5.68 mol) of 2-methoxymethyl-2-methyl-3-hydroxypropanal. The mixture was heated to 80° C. and stirred at that temperature for a further 2 hours. The mixture was then neutralized with formic acid, and the salt was removed by filtration. The product mixture was then distilled at up to the boiling point of 2-methoxymethyl-2-methyl-1,3-propanediol 2'-methoxymethyl-2'-methyl-3-hydroxypropionate (155° C./2 mbar) to give a first cut of 148 g.

The residue was taken up in 900 ml of methanol, 3.76 g (0.07 mol) of sodium methanolate were added, and the mixture was stirred at room temperature for 16 hours. Neutralization with acetic acid and subsequent distillation gave 312.8 (1.93 mol) of methyl 2-methoxymethyl-2-methyl-3-hydroxypropionate of boiling point 85°–95° C./8 mbar, corresponding to a 68% yield, based on starting 2-methoxymethyl-2-methyl-3-hydroxypropanal, and 249.7 g (1.86 mol) of 2-methoxymethyl-2-methyl-1,3-propanediol of boiling point 108°–109° C./8 mbar, corresponding to a 66% yield, based on starting 2-methoxymethyl-2-methyl-3-hydroxypropanal.

The methyl 2-methoxymethyl-2-methyl-3-hydroxypropionate was added at from 15° to 20° C. to 438 g (3.68 mol) of thionyl chloride, the temperature was then raised to 60° C. and the mixture was stirred until the evolution of gas had ended. Excess thionyl chloride was distilled off, 0.2 g (0.0025 mol) of pyridine was added to the residue, and the temperature was raised to 135° C. After the evolution of SO$_2$ had ended, distillation gave 317.0 g (1.76 mol) of methyl 2-methoxymethyl-2-methyl-3chloropropionate of boiling point 94° C. 35 mbar, corresponding to a 91% yield, based on methyl 2-methoxymethyl-2-methyl-3-hydroxypropionate.

We claim:

1. A process for preparing a 2,2-disubstituted 3-chloropropionic ester of the formula

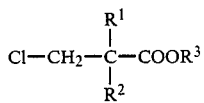

where $R^1$ and $R^2$ are each $C_1$–$C_6$-alkyl, $C_2$–$C_6$-oxaalkyl, $C_2$–$C_6$-alkenyl, $C_2$–$C_6$-oxaalkenyl, aryl, or $C_7$–$C_{12}$-aralkyl where $R^1$-C-$R^2$ together can also form a 5-, 6- or 7-membered ring, and where $R^3$ has the meanings of $R^1$ and $R^2$ other than aryl, which process comprises:

converting a 2,2-disubstituted 3-hydroxypropanal of the formula

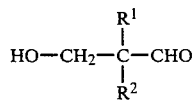

into the esterdiol

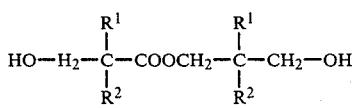

by disproportionation accordinng to the Tischenko process;

reacting this esterdiol III in the presence of a transesterification catalyst with an alcohol $R^3OH$ to give the 3-hydroxyester

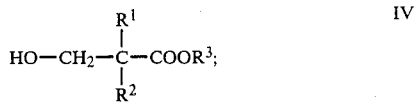

reacting the hydroxyester IV with a stoichiometric or greater than stoichiometric amount of thionyl chloride to form a chlorosulfinate intermediate; and thermally decomposing said chlorosulfinate intermediate at 120° to 180° C. to give the chloropropionic ester I.

2. A process as claimed in claim 1, wherein $R^3$ is methyl or ethyl.

3. A process as claimed in claim 1, wherein the transesterification catalyst used is an alkali metal alcoholate or an alkaline earth metal alcoholate.

4. A process as claimed in claim 1, wherein the alcoholate is used in an amount of from 0.01 to 0.1 mole per mole of esterdiol III.

5. A process as claimed in claim 1, wherein from 1 to 20 moles of alcohol $R^3OH$ are used per mole of esterdiol III.

6. A process as claimed in claim 1, wherein from 1 to 3 moles of thionyl chloride are used per mole of 3-hydroxyester IV.

7. A process as claimed in claim 1, wherein the reaction with thionyl chloride to form said chlorosulfinate intermediate is first carried out at from $-10°$ to $+60°$ C., and said thermal decomposition of said chlorosulfinate intermediate is then carried out at the elevated temperature of 120° up to 180° C.

8. A process as claimed in claim 7, wherein the reaction with thionyl chloride is carried out at from $-10°$ to $+50°$ C., and said thermal decomposition is then carried out at from 120° to 140° C.

9. A process as claimed in claim 7, wherein said thermal decomposition is carried out in the presence of a tertiary amine base.

10. A process as claimed in claim 1, wherein the alcohol $R^3OH$ is selected from the group consisting of methanol, ethanol, propanol, iso-propanol, n-butanol, iso-butanol, tert.-butanol, n-pentanol, iso-pentanol, n-hexanol, iso-hexanol, methoxyethanol, butoxyethanol, allyl alcohol, methallyl alcohol, benzyl alcohol and 2-phenylethan-1-ol.

11. A process as claimed in claim 1, wherein the alcohol $R^3OH$ is methanol.

* * * * *

UNITED STATES PATENT AND TRADEMARK OFFICE
CERTIFICATE OF CORRECTION

PATENT NO. : 4,837,357
DATED : June 6, 1989
INVENTOR(S) : Merger et al

It is certified that error appears in the above-identified patent and that said Letters Patent is hereby corrected as shown below:

IN THE ABSTRACT:

Please correct formula III by substituting the formula below:

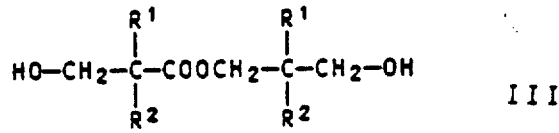    III

Please correct formula IV by substituting the formula below:

    IV

IN THE CLAIMS:

In Claim 1, at line 45-50, correct formula III by substituting the formula below:

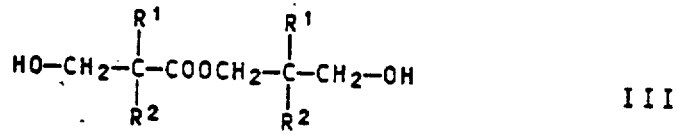    III

UNITED STATES PATENT AND TRADEMARK OFFICE
CERTIFICATE OF CORRECTION

PATENT NO. : 4,837,357

DATED : June 6, 1989

INVENTOR(S) : Merger et al.

Page 2 of 2

It is certified that error appears in the above-identified patent and that said Letters Patent is hereby corrected as shown below:

In Claim 1, at line 51, "accordinng" should be --according--.

Signed and Sealed this

Thirteenth Day of February, 1990

Attest:

JEFFREY M. SAMUELS

Attesting Officer

Acting Commissioner of Patents and Trademarks